(12) United States Patent
Balhorn et al.

(10) Patent No.: US 6,420,112 B2
(45) Date of Patent: *Jul. 16, 2002

(54) DNA ATTACHMENT TO SUPPORT STRUCTURES

(75) Inventors: Rodney L. Balhorn, Livermore; Christopher H. Barry, Fresno, both of CA (US)

(73) Assignee: The Regents of the University of California, Oakland, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/359,147

(22) Filed: Jul. 21, 1999

(51) Int. Cl.⁷ .............................. C12Q 1/68; C12M 1/34; G01N 33/566; C07K 16/00; C07H 21/00
(52) U.S. Cl. .............................. 435/6; 435/183; 435/7.1; 435/287.2; 436/501; 436/94; 530/387.1; 536/23.1; 536/25.32
(58) Field of Search .......................... 435/6, 91.1, 183, 435/194, 287.2, 7.1; 536/23.1, 25.32; 530/387.1; 436/501, 94

(56) References Cited

U.S. PATENT DOCUMENTS

| | | | |
|---|---|---|---|
| 5,122,600 A | 6/1992 | Kawaguchi et al. | 536/27 |
| 5,132,242 A | 7/1992 | Cheung | 436/501 |
| 5,194,300 A | 3/1993 | Cheung | 427/213.31 |
| 5,556,955 A | * 9/1996 | Vernaud et al. | 56/23.31 |
| 5,674,743 A | 10/1997 | Ulmer | 435/287.2 |
| 5,698,400 A | * 12/1997 | Cotton et al. | 435/6 |
| 5,710,028 A | * 1/1998 | Eyal et al. | 435/91.1 |
| 5,776,674 A | 7/1998 | Ulmer | 435/6 |

OTHER PUBLICATIONS

The Telomere Terminal Transferase of Tetrahymena Is A Ribonucleoprotein Enzyme With Two Kinds Of Primer Specificity, Carol W. Greider et al., Cell, vol. 51, 887–898, Dec. 24, 1997.

Deoxynucleotide–polymerizing Enzymes Of Calf Thymus Gland, Ken–Ichi Kato et al., The Journal Of Biological Chemistry, vol. 242, No. 11, Issue of Jun. 10, pp. 2780–2789, 1967.

Direct Mechanical Measurements of the Elasticity of Single DNA Molecules by Using Magnetic Beads, Steven B. Smith et al., Science, vol. 258, Nov. 13, 1992, pp. 1122–1126.

Ionic Effects on the Elasticity of Single DNA Molecules, Christoph G. Baumann, Et al., Proc. Natl. Acad. Sci. USA, vol. 94, pp. 6185–6190, Jun. 1997.

Overstretching B–DNA: The Elastic Response of Individual Double–Stranded and Single–Stranded DNA Molecules, Steven B. Smith et al., Science, vol. 271, Feb. 9, 1996, pp. 795–799.

Behavior of Supercoiled DNA, T.R. Strick et al., Biophysical Journal, vol. 74, Apr. 1988, pp. 2016–2028.

* cited by examiner

Primary Examiner—B. L. Sisson
(74) Attorney, Agent, or Firm—Eddie E. Scott; Ann M. Lee; Alan H. Thompson

(57) ABSTRACT

Microscopic beads or other structures are attached to nucleic acids (DNA) using a terminal transferase. The transferase adds labeled dideoxy nucleotide bases to the ends of linear strands of DNA. The labels, such as the antigens digoxigenin and biotin, bind to the antibody compounds or other appropriate complementary ligands, which are bound to the microscopic beads or other support structures. The method does not require the synthesis of a synthetic oligonucleotide probe. The method can be used to tag or label DNA even when the DNA has an unknown sequence, has blunt ends, or is a very large fragment (e.g., >500 kilobase pairs).

30 Claims, No Drawings

DNA ATTACHMENT TO SUPPORT STRUCTURES

The United States Government has rights in this invention pursuant to Contract No. W-7405-ENG48 between the United States Department of Energy and the University of California for the operation of Lawrence Livermore National Laboratory.

BACKGROUND OF THE INVENTION

1. Field of the Invention

This invention relates to a method for attaching nucleic acids, such as DNA, to microscopic beads or other support structures using a terminal transferase.

2. Description of Related Art

Recent technical advancements in nanomanipulation have allowed the mechanical behavior of single DNA molecules to be studied. These techniques include the use of microspheres, magnetic beads, microfibers, microneedles, optical traps, and hydrodynamic flow. The attachment of microspheres to DNA has proven useful to manipulate DNA for placement or immobilization on a selected substrate or mechanical support, where the DNA strand can be confined in an extended conformation. Once the DNA is affixed to a substrate, a variety of processes (e.g., laser tweezers, scanning probe microscopy) can be used to sequence or map gene locations of the DNA. In addition, tethering microspheres to DNA may be useful in purification or separation methods that selectively isolate labeled or tagged DNA fragments.

Conventional techniques of tethering or attaching DNA to microspheres rely on hybridization and ligation of manufactured, labeled single-stranded DNA probes to known DNA sequences. U.S. Pat. No. 5,674,743 to Ulmer discusses methods in the art for attaching the DNA to a microscopic bead and is incorporated herein by reference. One method is to first couple specific oligonucleotide linkers to the bead using known techniques, and then to use DNA ligase to link the DNA to the linker on the bead. Oligonucleotide linkers can be employed which specifically hybridize to unique sequences at the end of the DNA fragment, such as the overlapping end from a restriction enzyme site or the "sticky ends" of bacteriophage lambda based cloning vectors.

Another method for coupling DNA to beads uses specific ligands attached to the end of the DNA to link to ligand-binding molecules attached to the bead. Possible ligand-binding partner pairs include biotin-avidin/streptavidin, or various antibody/antigen pairs such as digoxygenin-antidigoxygenin antibody (Smith et al., "Direct Mechanical Measurements of the Elasticity of Single DNA Molecules by Using Magnetic Beads," Science 258:1122–1126 (1992)). Smith et al. (1992) describe the attachment of the ends of Lambda DNA fragments to magnetic beads and glass plates using ligated 97-kbp dimers of methylated phage DNA. The left sticky end of the dimer is hybridized and ligated to a 12-base oligo, 3' end-labeled previously with digoxigenin. The right sticky end is similarly attached to a 12-base oligo constructed with a 3' biotin end-label. The glass plates and beads were then labeled with antidigoxygenin and avidin/streptavidin, respectively. In this procedure, the sticky ends of the dimer are known, and the fragment of DNA is relatively small. Individual multimer of λ DNA (48.5 kbp) were chemically attached by one of their ends to a glass slide and by their other end to a magnetic bead. Ligated 97-kbp dimers of methylated phage λ DNA, strain c1857ind1Sam7 (NEB) were used. The left sticky end of the dimer is hybridized and ligated to a 12-base oligo. 3' end-labeled previously with digoxigenin (Boehringer Genius-5). The right sticky end is similarly attached to a 12-base oligo constructed with a 3' biotin end-label (Glenn Research). The glass microscope slide is successively coated with γ-aminopropyltriethoxysilane (Pierce), protein A, polyclonal antidigoxigenin (Boehringer), and finally cross-linked with dimethyl pimelimidate (Pierce). The molecule ends were labeled differently to prevent attachment of both ends of the DNA to either the glass of the bead. The DNA is free to swivel about either point of attachment.

In Baumann et al., "Ionic effects on the elasticity of single DNA molecules", Proc. Natl. Acad. Sci. USA 94:6185–6190 (1997), lambda phage DNA molecules are tethered between two streptavidin-coated latex beads (d=3.5 μm). One bead is held by a micropipette while the other is optically trapped by force-measuring laser tweezers. The 5'-overhangs of λ DNA were biotinylated with the Klenow fragment of DNA polymerase using biotin-11-dCTP (Sigma), dATP, dGTP, and dUTP. The Klenow fragment is the E. coli DNA polymerase I fragment. The polymerase catalytically synthesizes new strands of DNA in vitro by moving along the preexisting single DNA strand and creating a new complementary strand by incorporating single nucleotides one at a time into the new strand. λ-DNA molecules were tethered between two streptavidin-coated latex beads (diameter b 53.54mm). One bead was held by a micropipette while the other was optically trapped by force-measuring laser tweezers.

The 5'-overhangs of 1 DNA (methylated c1857ind1Sam7; New England Biolabs) were biotinylated with the Klenow fragment of DNA polymerase using biotin-11-dCTP (Sigma), dATP, dGTP, and dUTP . . . Single-strand nicks were repaired with DNA ligase. After biotinyla-tion and nick ligation, DNA stocks were stored in an EDTA-containing buffer.

In Smith et al., "Overstretching B-DNA: The elastic response of individual double-stranded and single-stranded DNA molecules", Science 271:795–799 (1996), the DNA was labeled at both ends. Two oligonucleotides were constructed: a 20-nucleotide strand complementary to the right overhand of λ, and a 5'-biotinylated 8-nucleotide complementary to the remaining 8 base pairs of the 20-nucleotide fragment. These oligos were hybridized to each other and to the right end of λ, and then ligated with T4 ligase. The left end of λ was then biotinylated with Klenow enzyme and bio-11-dCTP. Each end of a single λ-phage dsDNA molecule (48.5 kbp) was attached to a separate microscopic latex bead. Carboxylate-polystyrene beads (3.54 μm in diameter, CV=2.7%, Spherotech) were covalently coated with streptavidin using 1-ethyl-3-(3-dimethylaminopropyl) carbodiimide (EDAC). Each molecule was pulled both right and left from the pipette to determine the point of attachment of the molecule on the pipette bead. DNA molecules are compact random coils in solution except when one attaches by an end to the bead on the pipette tip. Extra beads are carried by buffer and one is caught by the laser trap.

In Strick et al., "Behavior of Supercoiled DNA", Biophysical Jour. 74:2016–2028 (1998), linear DNA molecules (60-kb) were bound to strepavidin-coated superparamagnetic beads. A segment of photochemically labeled DNA was affixed to each end of a 48.5-kb phage λ DNA. A 5-kb fragment tagged roughly every 200–400-bp with a biotin label was annealed and ligated to the cohesive left end of the λ-DNA with T4 DNA ligase. A 6-kb fragment was similarly tagged with digoxigenin molecules, and then annealed and ligated to the cohesive right end of the λ-DNA. Fifty micrograms of phage 1-DNA (Boehringer-Mannheim, Meylan, France) are recipitated and resuspended in distilled water to eliminate any organic buffers. Two batches of this DNA are aliquoted; the first is subjected to two successive rounds of photolabeling in the presence of 25 mg of photoactivatable biotin (Pierce, Montlucon, France). Photolabeling reactions are carried out according to the Pierce protocol: DNA at a concentration of 1 mg/ml is mixed with an equal volume of photobiotin (also at a concentration of 1 mg/ml). The reaction tube is left open and placed in an ice bath, 10 cm away from a 40-W, 360-nm sunlamp for 10 min. The process is repeated, with the addition of another 25 ml of photobiotin. A second aliquot of purified DNA is subjected to the same sequence of labeling reactions, except that photoactivatable digoxigenin (Boehringer-Mannheim) is used as the labeling molecule. Both batches of labeled DNA are then precipitated in cold ethanol and resuspended in Tris-HCl (10 mM) and EDTA (1 mM) (T10 E1). They are then digested by 10 units of restriction enzyme Nru1 (New England Biolabs, Montignyle-Bretonneux, France) at 37° C. in the enzyme's buffer. The cohesive left (4600 bp) and cohesive right (6700 bp) fragments are isolated on an ethidium-bromide free, 0.6% agarose gel in 13 Tris-acetate-EDTA (TAE) running buffer. They are then purified with the GeneCleanII system (Bio101, France), precipitated in cold ethanol and resuspended in 10 ml of T10E1. The cohesive-left biotin-labeled fragments are then annealed for 24 h at 37° C. to intact 1-DNA molecules suspended in T10E1 and 10 mM MgCl2, and ligated for 1 h at 37° with 5 units of T4 DNA ligase (Boehringer-Mannheim). The cohesive-right digoxigenin-labeled fragments are annealed and ligated to the reaction product in an identical manner. The final construction is thus 59.8 kb long, with biotin and digoxigenin end-labels making up 11.3 kb.

Approximately 107 DNA molecules are incubated in 10 ml PBS with 8 ml of streptavidin-coated superparamagnetic beads (Dynal M280 or M450), previously washed three times in PBS. The reaction is stopped after 5 min by the addition of 90 ml of standard solution (10 mM PB pH 8, 0.1% Tween, 0.1 mg/ml FS DNA, and 3 mM NaN3, referred to hereafter as 10 mM PB or 10 mM phosphate buffer). Twenty microliters of that mnix is further diluted in 80 ml of standard solution and injected into the capillary tube. As the beads sediment to the capillary's "floor," they bring the DNA molecules in contact with the antidigoxigenin-coated surface. The bead-DNA constructs are then left to incubate for at least 2 h before studies begin. We can increase the number of supercoilable (unnicked) molecules by performing a ligation reaction with T4 DNA ligase, either before or after the bead-DNA complex is injected into the capillary.

Covalent chemical attachment of the DNA to the bead can be accomplished by using standard coupling agents to link the 5'-phosphate on the DNA to coated microspheres through a phosphoamidate bond. In a particular embodiment in which the DNA contains the appropriate single-stranded telomeric recognition site, telomere terminal transferase (Greider et al., Cell 51:887–898 (1987)) can be used to incorporate a biotinylated nucleotide at the 3' end of the DNA which can then be bound to avidin immobilized on the bead. The only substrates required for the reaction are a single-stranded telomeric sequence oligonucleotide, and dGTP plus dTTP. Repeats of the Tetrahymena telomeric sequence TTGGGG are added, 1 nucleotide at a time, onto the 3' end of the input primer. A standard assay contained 20 µl of a 2×reaction mix and 20 µl of an enzyme fraction. The 2×reaction mix consisted of 4 µl of 10×reaction buffer, 20 mM dTTP, 2 µM dGTP, 0.8 µg (TTGGGG)$_4$ oligonucleotide (unless some other oligonucleotide was specified), 0.5 U of RNasin, and 1 µl(10 µCi of [α-$^{32}$P]dGTP (specific activity, 3000 Ci/mmol). The 10×reaction buffer contained 500 mM Tris (pH 8.5), 1 M sodium acetate, 20 mM MgCl$_2$. 1 mM spermnine, 10 mM spermidine, and 50 mM 2-mercaptoethanol. After mixing the enzyme preparation to be assayed with the reaction mix, samples were incubated at 30° C. for 60 min. In another embodiment, calf thymus terminal transferase (Kato et al., J. Biol. Chem. 242:2780 (1967)) can be used to incorporate a ligand-linked nucleotide onto the 3' end of any DNA molecule with a free 3' hydroxyl group. In still another approach, a DNA-binding protein can be coupled to the bead by chemistries well known in the art and in such a fashion that the DNA-binding site is unperturbed. DNA containing the recognition sequence for the DNA-binding protein can thereby be coupled to the bead. When incubations are carried out in phosphate buffer, the terminal transferase has an absolute requirement for an oligodeoxynucleotide initiator containing at least three phosphate groups and a free 3' hydroxyl. Reaction mixtures (1.0 ml) contained 40 mM potassium phosphate (pH 7.0), 8 mM MgCl$_2$, 1 mM mercaptoethanol, 2 mM dATP, 20 µg of terminal transferase protein, and the $^3$H-labeled initiator listed. After overnight incubation at 35°, each reaction mixture was filtered through a Sephadex G-75 column (2.5×40 cm) equilibrated with 10 mM NaCl.

As an alternative to microscopic beads, bead-like structures referred to as "optical handles" can be chemically synthesized at the end of a DNA molecule to provide a particle with dimensions and refractive properties appropriate for manipulation by an optical trap. The first step in the synthesis of such particle-like structures at the end of a DNA molecule can be accomplished by methods similar to those described above, with the sequential addition of branched oligonucleotides or by modification of the techniques for the synthesis of starburst dendrimers.

In general, the first step in the synthesis of an "optical handle" at a specific target sequence requires the binding of a bifunctional binding agent to the target sequence. The first functionality of the binding agent provides a means for uniquely recognizing and binding to the target DNA sequence. The second functionality provides a means for binding or linkage to initiate the first cycle of growth of the optical handle. Such functionality, for example, can be provided by a biotin group attached to the DNA recognition and binding functionality so as to be capable of binding to streptavidin. Adding streptavidin to the bifunctional binding agent already complexed with its target DNA sequence then results in a complex composed of target DNA, bifunctional linker-biotin, and streptavidin. Streptavidin contains four binding sites for biotin, with two each on opposite sides of the streptavidin protein molecule. Only one of these sites will be occupied by binding to the biotin group of the bifunctional linker, leaving the three other sites available for binding.

A second linker is introduced which is made of two biotin molecules joined by a spacer. The spacer couples the two biotin groups in such a way that each biotin is fully capable of binding to streptavidin, but the length and rigidity of the spacer is selected so that both biotin groups cannot bind to the same streptavidin molecule. Addition of biotin-spacer-biotin to the complex will result in the binding of one, two or three such molecules to the previously unoccupied sites in the single streptavidin molecule, providing one, two or three exposed biotin groups for subsequent binding to additional streptavidin molecules. By alternating the addition of streptavidin and biotin-spacer-biotin, the optical handle is synthesized as an exponentially growing complex of cross-linked streptavidin molecules. A sufficient number of cycles are carried out to provide an optical handle of sufficient size and optical properties for manipulation by optical tweezers.

One of the disadvantages of the above techniques for attaching DNA to microscopic beads or other structures is that the sequence at the end of the DNA fragment must be known in order to synthesize an oligonucleotide linker or probe. Thus, completely unknown DNA fragments cannot be attached to microspheres or supports using these methods. In addition, if small (<18 bp) synthesized oligonucleotides are used, these oligonucleotides can attach to the targeted sequence within large DNA fragments, e.g., >500-kb, not just at the ends. Finally, the hybridization attachment methods are limited to DNA fragments with cohesive, single-strand ends.

The present invention addresses the above-mentioned problems and provides a simple method for attaching microscopic beads and other particle-like (e.g., optical handles) or support structures to fragments of DNA of unknown sequences, of any length, and having either single-stranded or blunt (double-stranded) ends. The present method is capable of labeling both ends of the double-stranded DNA, differentiating one end from the other, and labeling the ends independently of sequence and regardless of 3' or 5' recessive ends. The present invention also provides for a covalent tethering of both DNA ends with an appropriate cross-linker and does not require the synthesis of a synthetic oligonucleotide probe.

SUMMARY OF THE INVENTION

The object of the invention is to attach nucleic acids, specifically DNA, to microscopic beads or other support structures using a terminal transferase. The present invention accomplishes this attachment without the synthesis of oligonucleotide probes or known target oligonucleotide or amino acid sequences.

In the present method, DNA is placed in solution with labeled dideoxy nucleotide bases. Nucleotides with antigen labels such as digoxigenin and biotin may be used. When linear double-stranded DNA is present, terminal transferase is added, which attaches a single labeled base to each of the 3' ends of the DNA strands. When two different labeled bases are used (e.g., digoxigenin and biotin), the yield of DNA strands with different labels on the ends is predictably 50%. The differently labeled ends prevent both ends of a single DNA molecule from attaching to a single support structure. The labeled DNA is attached to the microscopic beads or other support structures, which are labeled with the appropriate antibody (e.g., anti-digoxigenin or avidin/streptavidin) or other complementary ligand.

Another object of the present invention is to provide a method that can be used with DNA strands having blunt (double-stranded) or single-stranded (cohesive, sticky) ends. Furthermore, the invention can attach microscopic beads, bead-like structures such as optical handles, or other support structures to DNA of any size, including fragments greater than 500 kilobase pairs (kb).

Other objects, features, and advantages of the present invention will become apparent from the following description and accompanying drawings.

DETAILED DESCRIPTION OF THE INVENTION

The present invention is a method for attaching microscopic beads or other structures to nucleic acids using a terminal transferase. The present method is particularly useful for attaching microscopic structures to DNA. The microscopic structures include microspheres and microscopic beads made from latex, polystyrene, and magnetic or paramagnetic materials. Other structures include substrates made of glass, mica, or silicon materials. The present method can be used to tag or label DNA even when the DNA has an unknown sequence, or is very large (e.g., >500 kilobase pairs). The present invention does not require the synthesis of a synthetic oligonucleotide probe.

In the present method, DNA is added to a buffered solution containing labeled dideoxy nucleotide bases, an enzyme, and the salts and metals needed for the enzyme to be chemically active. The bases are typically labeled in equal molar amounts with two different labels, such as the antigens digoxigenin and biotin. The labels can bind to the antibody compound (e.g., anti-digoxigenin or avidin/streptavidin) or other appropriate complementary ligand to form a tight or strong bond. The antibodies or ligands are bound to the microscopic beads or support structures by methods known in the art. Two different labels are typically used so that both ends of the DNA strand do not attach to the microscopic bead or other support structure. Many types of labels can be used: fluorescent labels, bioreactive labels, chemiluminescent labels, photolabile labels, photoreactive labels, radioactive labels, and chemically reactive labels.

When linear double-stranded DNA is formed, such as by heating, terminal transferase is added to the DNA solution. Terminal transferase is a calf thymus enzyme that adds one labeled nucleotide to each 3' end of the DNA strands and provides a method for creating cohesive ends on blunt-ended DNA fragments. The labeled nucleotide is added independent of sequence or whether the strands have overhangs (single-stranded) or blunt (double-stranded) ends. Since the nucleotides add randomly to the ends, the two labels have equal probability of attaching to each end. Thus, fifty percent of the labeled DNA strands have different labels at the ends.

Since the transferase adds the bases at the ends of the DNA strands, there is labeling along the strand unless there is a break in the DNA. The present invention can easily be used with large DNA sequences, for example, greater than 500 kb. This lack of "intra-strand" labeling can be a distinct advantage of the present invention over conventional techniques. Conventional techniques that depend on hybridizing short oligonucleotide sequences (5–20 bases) that can occur (be repeated) elsewhere along the strand (as well as at the end) may result in undesirable intra-strand labeling. Indeed, the longer the DNA sequence and the shorter the synthesized oligonucleotide (e.g., <18 bp), the more likely the target sequence will be present within the molecule. Thus, conventional techniques may produce unsatisfactory results with large DNA sequences.

After the reaction is completed, the excess nucleotides are removed and the DNA is purified of the label. The 50% yield of DNA strands that have the same label on both ends are removed by binding the strands first to beads or resin with avidin and washing off with biotin. The beads (or resin) are then bound with antibody to digoxigenin. Only those strands having both (different) labels will bind the second time. The dual-labeled DNA is then mixed with the microscopic beads or other support structures that are coated or otherwise bound to the complementary ligand. The end of each DNA strand with the complementary ligand forms a covalent bond with bead or support structure. The non-attached end of the DNA, having a different label, can then be attached to microscopic beads or support structures that are coated or otherwise bound to a second complementary ligand.

EXAMPLE

Terminal Transferase Labeling of Lambda DNA

The Lambda DNA molecule (Gibco) is added to a buffer solution containing components required for enzyme activity (e.g., enzyme and salts/metals) and dideoxy nucleotide bases labeled in equal molar amounts with two antigens, such as digoxigenin or biotin. The solution is heated to denature the cos site of Lambda, which creates linear double-stranded DNA. Terminal transferase is added and the solution is heated for one or more hours. The transferase adds one nucleotide at the 3' end of each of the DNA strands before the reaction is arrested. The nucleotide is added independent of sequence or whether the strands have overhangs or blunt ends. The nucleotides will add randomly to the 3' ends, so either ddNTP-DIG or ddNTP-BIO has an equal opportunity of binding to either end of the DNA. Thus, there is an acceptable yield of 50% labeled DNA fragments containing the digoxigenin label at one end and a biotin on the other.

After the excess nucleotides are removed and the DNA is purified of contaminated label, the DNA is attached to spheres coated with the complementary antibody. This provides a covalent tethering of both DNA ends with an appropriate cross-linker. The antibodies are attached to the spheres by methods known in the art.

The foregoing description of preferred embodiments of the invention is presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated.

What is claimed is:

1. A method for attaching double-stranded DNA to a support structure, comprising:
   providing a mixture of a plurality of linear double stranded DNA molecules and an excess plurality of labeled dideoxy nucleotides bases;
   adding terminal transferase to said mixture, wherein said transferase binds said labeled dideoxy nucleotide bases to at least one 3' end of a double-stranded DNA molecule forming a plurality of a labeled double-stranded DNA molecules and a plurality of unbound bases;
   removing said unbound bases from said mixture; and
   adding said mixture a plurality of support structures, wherein each structure comprises a first ligand that binds to said labeled DNA, wherein upon said addition said plurality of support structures binds to said labeled double-stranded DNA molecules.

2. The method as cited in claim 1, wherein the nucleotide bases are labeled in equal molar amounts with a first label and a second label.

3. The method as recited in claim 2, wherein at least one of the labels comprises biotin.

4. The method as recited in claim 2, further comprising removing strands from the mixture having both 3' ends of said double stranded DNA molecules labeled with the same label before adding the support structures.

5. The method as recited in claim 4, further comprising adding to said mixture a plurality of support structures comprising a second ligand that binds to the other 3' end of said labeled DNA, wherein each of the 3' ends is bound to a different support structure.

6. The method as recited in claim 2, wherein at least one of the labels comprises an antigen.

7. The method of claim 6, wherein said first ligand comprises an antibody.

8. The method as recited in claim 6, wherein said first ligand comprises an antibody capable of binding to said antigen.

9. The method of claim 8, wherein the antigen is digoxigenin and the antibody in antidioxigenin.

10. The method as recited in claim 1, wherein the linear double-stranded DNA molecules comprises blunt ends.

11. The method as recited in claim 1, wherein the linear double-stranded DNA molecules comprises single-stranded ends.

12. The method as recited in claim 1, wherein the linear double-stranded DNA molecules comprise DNA having at least 500,000 base pairs.

13. The method as recited in claim 1, wherein the linear double-stranded DNA molecules comprises DNA having ends of unknown sequence.

14. The method as recited in claim 1, wherein the support structures are selected from the group consisting of beads, flat substrates, and microspheres.

15. The method as recited in claim 1, wherein the support structures comprise materials selected from the group consisting of latex, polystyrene, magnetics materials, paramagnetic materials, glass, mica, and silicon.

16. A method for attaching double-stranded DNA to a support structure, comprising:
   providing a mixture of a plurality of linear strands of double-stranded DNA molecules having at least 500,000 base pairs and an excess of labeled dideoxy nucleotide bases;
   adding terminal transferase to said mixture, wherein said tranferase binds said labeled dideoxy nucleotide bases to at least on 3' end of a strand forming a plurality of labeled double-stranded DNA molecules and a plurality of unbound bases;
   removing said unbound bases from said mixture; and
   adding to said mixture a plurality of support structures, wherein each structure comprises a first ligand that binds to one end of said labeled DNA, wherein upon said addition said plurality of support structures binds to said labeled double-stranded DNA molecules.

17. The method of claim 16, wherein the dideoxy nucleotide bases are labeled in equal molar amounts with a first label and a second label.

18. The method as recited in claim 17, wherein at least one of the labels comprises biotin.

19. The method of claim 17, further comprising removing strands from the mixture having both 3' ends of said double-stranded DNA molecule labeled with the same label before adding the support structures.

20. The method of claim 19, further comprising adding to the mixture a plurality of support structures comprising a second ligand that binds to the other 3' end of said labeled DNA, wherein each of the 3' ends is bound to a different support structure.

21. The method of claim 17, wherein at least one of the labels comprises an antigen.

22. The method of claim 21, wherein said first ligand comprises an antibody.

23. The method of claim 21, wherein said first ligand comprises an antibody capable of binding to said antigen.

24. The method of claim 23, wherein the antigen is digoxigenin and the antibody is anti-dioxigenin.

25. The method of claim 16, wherein the linear strands of double-stranded DNA molecules comprise blunt ends.

26. The method of claim 16, wherein the linear strands of double-stranded DNA molecules comprise single-stranded ends.

27. The method of claim 16, wherein the linear strands of double-stranded DNA molecules comprise DNA having ends of unknown sequence.

28. The method of claim 16, wherein the support structures are selected from the group consisting of beads, flat substrates, and microspheres.

29. The method of claim 17, wherein the support structures comprise materials selected from the group consisting of latex, polystyrene, magnetic materials, paramagnetic materials, glass, mica, and silicon.

30. A method for attaching double-stranded DNA to a support structure, comprising:

providing a mixture of a plurality of linear strands of double-stranded DNA molecules having at least 500,000 base pairs and an excess plurality of labeled dideoxy nucleotide bases wherein the nucleotide bases are labeled in equal molar amounts with a first label and a second label;

removing said unbound bases from said mixture;

removing strands of double-stranded DNA molecules from the mixture having both ends labeled with the same label; and adding to said mixture a plurality of support structures, wherein each structure comprises a first ligand that binds to one end of said labeled DNA and a second ligand that binds to the other end of said labeled DNA, wherein upon said addition said plurality of support structures bind to said labeled double-stranded DNA molecules.

* * * * *